United States Patent [19]

Rauleder et al.

[11] Patent Number: 4,987,268

[45] Date of Patent: Jan. 22, 1991

[54] PROCESS FOR THE PREPARATION OF ASYMMETRIC TERMINALLY MONO-UNSATURATED GLYCOL ETHERS

[75] Inventors: Hartwig Rauleder; Hans-Joachim Kötzsch, both of Rheinfelden; Hans-Joachim Vahlensieck, Wehr, all of Fed. Rep. of Germany

[73] Assignee: Huels Aktiengesellschaft, Marl I, Fed. Rep. of Germany

[21] Appl. No.: 491,774

[22] Filed: Mar. 12, 1990

[30] Foreign Application Priority Data

Mar. 17, 1989 [DE] Fed. Rep. of Germany ....... 3908792

[51] Int. Cl.$^5$ .................... C07C 41/05; C07C 41/06
[52] U.S. Cl. .................................. 568/616; 568/673
[58] Field of Search ................................ 568/616, 673

[56] References Cited

U.S. PATENT DOCUMENTS 2,841,621 7/1958 Riley .................................. 568/616
4,098,713 7/1978 Jones .................................. 568/616

*Primary Examiner*—Howard T. Mars
*Attorney, Agent, or Firm*—Felfe & Lynch

[57] ABSTRACT

Monoalkylethers of alkyleneglycols and oligoalkyleneglycols are reacted completely with terminally unsaturated alkenyl halides to form terminally mono unsaturated glycolethers as product, wherein initially a complete reaction to the corresponding alcoholate takes place with only one equivalent of alcoholate former, such as alkali metal alcoholate or hydroxide, and two equivalents of glycolmonoether, then the alcoholate is reacted with one equivalent of alkenyl halide, whereupon a mixture of the desired product and the glycolmonoether of the alkali metal halide is filtered or distilled off, then this mixture is reacted with the second equivalent of the alcoholate former, whereupon the recovery of the product takes place by distillation from the reaction mixture and then, after addition of a further equivalent of glycolmonoether to the residue from the product recovery, the reaction of the first and the subsequent steps is repeated.

4 Claims, No Drawings

PROCESS FOR THE PREPARATION OF ASYMMETRIC TERMINALLY MONO-UNSATURATED GLYCOL ETHERS

FIELD OF THE INVENTION

This invention relates to a process for the preparation of asymmetric terminally mono unsaturated glycol ethers of the formula $$R_1-(O-R_3)_n-OR_2 \quad (I)$$

wherein
$R_1$ is straight or branched alkyl of 1 to 4 carbon atoms,
$R_2$ is terminally unsaturated alkenyl of 2 to 6 carbon atoms, optionally methyl- or ethyl-substituted,
$R_3$ is identical or different alkylene groups of 2 to 4 carbon atoms, optionally methyl- or ethyl-substituted, and
n is an integer from 1 to 6, inclusive,
by converting a monoalkyl ether of the formula $$R_1-(O-R_3)_n-OH \quad (II)$$

wherein $R_1$, $R_3$ and n have the meanings previously defined, into an alcoholate with the aid of an alkali metal or alkaline earth metal or an alcoholate, oxide, hydride or hydroxide thereof, and subsequently reacting the alcoholate with a terminally unsaturated alkenyl halide of the formula $$X-R_2 \quad (III)$$

wherein
X is chlorine, bromine or iodine, and
$R_2$ has the meanings previously defined.

BACKGROUND OF THE INVENTION

The preparation of pure compounds of the formula (I) with acceptable yields by the Williamson Synthesis failed heretofore because of the formation of azeotropic mixtures of (I) with the starting materials of the formula (II). Despite large expenditures of distillation energy, which is of disadvantage, small amounts of pure (I) in addition to large amounts of mixtures of (I) and (II) which are unsuitable for further processing have always been obtained. Attempts to form the alcoholate completely without the use of an excess of (II) and to avoid the occurrence of the azeotrope remained unsuccessful. Very long reaction times lead, moreover, to side reactions and losses in yield. The starting compound (II) could not be reacted completely according to the prior art methods.

DESCRIPTION OF THE INVENTION

These difficulties are overcome in simple manner by the process according to the invention. In contrast to the prior art, the process according to the invention leads in the alcoholate step with an excess of (II) rapidly and under mild conditions to complete conversion into the alcoholate, and after its reaction with (III) to a mixture of (I) and (II) in which the total (II)—as a result of further initially only partial conversion to the alcoholate—is surprisingly bound in non-volatile form, so that (I) present in the mixture can be distilled out of the reaction as a pure product. The (II)-alcoholate remains therein intact and is suitable for the production of further (I) after completing the formation of (II)-alcoholate by addition of further (II).

In this way, the product of the formula (I) is obtained with very high, approximately quantitative yields as a pure product which, as a rule, is already so pure that it no longer needs to be further distilled.

The object of making available such terminally monounsaturated asymmetric α,ω-glycolalkylalkenyl ethers industrially in economical manner, results from the significance thereof as starting materials for hydrosilation products which are produced by addition of hydrogensilanes to the double bond. These hydrosilated asymmetric glycol ethers impart important properties to hydraulic fluids.

The subject of the invention is a process for the production of the indicated asymmetric ethers (I) from the alcoholates of the monoalkylethers (II) by reaction with alkenyl halides (III), wherein (a) initially two equivalents of (II) are reacted with one equivalent of the alcoholate-forming metal component until its complete conversion, under exclusion of oxygen, while the respective labile group is distilled off, (b) the (II)-alcoholate formed thereof is reacted completely with one equivalent of (III), (c) the obtained mixture of substances (I) and (II) is filtered off from precipitated metal halide or is distilled off completely, (d) the distillate or filtrate is reacted with a second equivalent of the alcoholate former under the conditions of (a), (e) then the product (I) is distilled off to a large extent and (f) a further equivalent of (II) is added to the alcoholate-containing reaction mixture remaining behind after the recovery of (I), the reaction according to (a) is taken to completion, and the process steps (a) to (e) are carried out again.

The process has the characteristic that frequently process steps (a) to (e) are repeated according to (f) at least several times.

The starting compounds (II) are monoalkylethers of alkyleneglycols and their condensation products, the oligoglycols, which for their part are homogeneous ethers of the indicated alkyleneglycols connected by oxygen bridges. Such starting compounds are; for example, 1-methoxypropanol-2; 2-methoxypropanol-1; dipropyleneglycolmonoethyl-, -n-propyl-, -iso-propyl- or the isomericbutyl ethers; 1-ethoxypropanol-2; 1-n- or iso-propoxypropanol-2; 2-sec.butoxypropanol-2; tripropyleneglycol-monomethylether; methyl-, ethyl-, n- and isopropyl-, sec. or tert.butyl-monoglycol, -diglycol or -triglycol; tetraethyleneglycolmonomethylether, penta- or bexaethyleneglycolmonomethylether or the corresponding monoethers of butylene- or dibutyleneglycols.

The common feature of these starting compounds is that they are already etherified by a lower alkyl radical at one end of the monoglycol or polyglycol chain. According to the instant process, they are converted into the alcoholate of the free OH— group by reaction with alkali metals, preferably sodium or potassium, or with alkaline earth metals like calcium, or their hydrides, oxides, alcoholates, or alkali metal hydroxides, either as solids or dissolved in water. Alcoholates, especially methylates or ethylates, and hydroxides of sodium or potassium are preferred. The labile groups are: hydrogen in the case of alkali metals and hydrides; alcohols in the case of alcoholates; and water in the case of hydroxides. The glycol monoalkylethers (II) which are converted into their alcoholates are reacted with alkenyl halides of the formula (III), for example with allyl chloride, allyl bromide, allyl iodide, methallyl chloride, vinyl chloride or bromide, 4-chlorbutene-1, 5-chlorpente-1 or 6-chloro, bromo- or -iodo-hexene-1. Preferred alkenyl halides are ally chloride, methallyl chloride, vinyl chloride or the corresponding bromides.

The asymmetric terminally unsaturated glycol ethers of the formula (I) produced by the process of the instant invention are, for example, 1-methoxy-, -ethoxy-, -n- or -iso-propoxy-, -n-, -iso-, -sec. or -tert.butoxypropyl-2-vinyl-, -allyl- and -methallyl-ether; 2-methoxy-, -ethoxy, -n- or -iso-propoxy-, -n-, -iso-, -sec. and -tert.butoxypropyl-vinyl- or -allyl-, or -methallyl-1-butenyl ether, -pentenyl ether or -hexenyl ether; dipropyleneglycol-monomethyl-monovinyl- or -allyl- or -methallyl or -1-butenyl ether; tripropyleneglycol-monomethyl-monovinyl- or -allyl- or -methallyl ether; mono-, di-, tri-, tetra-, penta- and hexaethyleneglycol-monomethyl-, -ethyl-, -n-, or -iso-propyl, -n-, -iso-, -sec. or tert.butyl-monovinyl, -allyl-, -methallyl-, -1-butenyl-, -pentenyl- or hexenyl ether or the butylene- and dibutylene-monoalkyl-monovinyl ether or -methyl-allyl ether. Preferred starting compounds of the formula (II) are the monoalkyl ethers of oligoalkyleneglycols, namely of diethyleneglycol, triethyleneglycol and tetraethyleneglycol as well as of monomeric ethyleneglycol.

The process of the present invention is preferably carried out in a reactor which is equipped with a stirrer which allows the addition of suspensions or pourable solids. The reactor may be equipped with a reflux condenser with distillate withdrawal means, vapor condenser, vacuum connections and controllable heating. In order to exclude oxygen, a blanket of nitrogen is provided. During the removal of the labile group, the boiling state must be maintained continuously, possibly under reduced pressure.

During the binding of the excess starting compound (II) as or to the alcoholate before the distillative separation of the product (I) from the reaction mixture and during the distillation of the product (I), a temperature limitation to a maximum of 130° C., preferably to 110° C., should be maintained throughout all process steps.

The limitation of the temperature according to the invention is an effective protection against undesired isomerizations of the terminally unsaturated groups which are present, for example allyl, 1-butenyl or methallyl groups of the products into the cis-trans-propenyl, or the isobutenyl ethers. We found that this rearrangement is induced thermally. This temperature limitation requires control measures for the continuous boiling reaction conditions when carrying out the alcoholate step. The control is effected by means of the use of sub-atmospheric pressure set according to the boiling behavior of the reaction mixture and/or with the aid of an inert solvent suitable for boiling point adjustment, from the group hydrocarbons, such as toluene, isooctane, the xylene isomers, like mesitylene, aromatic petroleum ethers with defined boiling points, etc. The solvents can serve at the same time as entraining media for the labile groups and as diluents in the separation of the metal halides by filtration. At the beginning of the reactions, the starting compound (II) is preferably provided together with the alcoholate former (2:1 equivalents).

The boiling condition is preferably adjusted with the aid of sub-atmospheric pressure and/or a solvent. The labile group must be completely distilled off.

The liquid mixture of (I) and (II) which is filtered off or distilled off is recycled into the reactor. Before the recovery of product (I) there is no need for complete reaction of the alcoholate former to take place; it is completed after the recovery of the product. After the recovery of the product, the process can be terminated by neutralization of the alcoholate remaining behind in the reactor.

The utilization of the unsaturated glycol ethers of the formula (I) takes place by conversion into special silanes by addition of hydrogenalkoxysilanes.

Products of the formula

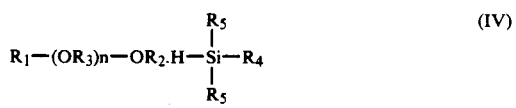

wherein
$R_1$, $R_2$, $R_3$ and n have the meanings previously defined,
$R_4$ is $R_1-O-$ or $R_1-(OR_3)_n-O-$, and
$R_5$ is $R_1$ or $R_4$, are produced.

These products are components of hydraulic fluids which are known from German Patent No. (DE-PS) 2 652 719, but are obtained in usable purity only as a result of the hydrosilation of compounds of the formula (I).

The following examples illustrate the present invention and will enable others skilled in the art to understand it more completely. It should be understood, however, that the invention is not limited solely to the particular examples given below.

EXAMPLE 1

1-Methoxy-2-methallyloxypropane (A) Synthesis 1803 g (20 mols) of 1-methoxypropanol-2 and 540 g (10 mols) of solid sodium methylate were introduced into a 4-liter cylindrical vessel with a fixed stirrer equipped with peripheral flow divider, provided with a thermostatically heated double jacket, 6-plate filled column, $N_2$-blanket, distillation arrangement and vacuum production. Upon heating the contents to 124° C., 220 g of methanol distilled off within 60 minutes, and the sodium methylate went completely into solution. A further 74 g of methanol were distilled off via a column under like conditions within one further hour. Then distillate withdrawal was terminated, the reaction mixture was cooled to 60° C. and refluxed at this temperature and 50 mbar sub-atmospheric pressure for 1 hour, whereby a residual 21 g of methanol escaped from the reaction mixture via the reflux condenser and were captured in the cooling trap of the vacuum producer operating at −80° C. After no more methanol was detectable in the reaction mixture and in the reflux condensate, 906 g (10 mols) of methallyl chloride were metered into the reactor within 100 minutes while stirring and thermostatically cooling to 60° C. The exothermic reaction increased the temperature in the reactor to 104° C. Sodium chloride precipitated. Further stirring took place for 70 minutes at 110° C. Then the column was exchanged for a distillation attachment for molecular distillation, and the mixture consisting almost exactly of 10 mols each of 1-methoxypropanol-2 and 1-methoxy-2-methallyloxypropane was distilled off from the NaCl precipitate first at 90°0 C./100 mbar, then at a pressure reduced to 10 mbar with falling boiling point and the NaCl was finally dried at 1 mbar, with the remainder of the produce being captured in the cooling trap.

Altogether, 2336 g of distillate composed of 62% by weight 1-methoxy-2-methallyloxypropane and 39% by weight 1-methoxypropanol-2 were obtained. 580 g of dry, pourable NaCl were emptied out of the reactor.

(B) Isolation

The reactor described in (A) was charged with the 2336 g of final distillate from process sequence (A) and with 540 g (10 mols) of solid sodium methylene. Upon heating of the contents to 124° C., 220 g of 1methanol distilled off within 60 minutes, and the sodium methylate went into solution. Upon distillation at 90° C./100 mbar, a further 29 g of methanol passed over. Then the release of methanol ceased. Even boiling of the reaction mixture at 70° C./20 mbar caused only traces of methanol to collect in the cooling trap. Then the column was exchanged for a distillation attachment for molecular distillation, and the reaction mixture was distilled at a boiling point of 70° C./20 mbar until, when the reactor temperature had again increased to 120° C., nothing more passed over. 1368 g of pure 1-methoxy-2-methallyloxypropane were obtained, which corresponds to a pure yield of 94–95%, based on 10 mols each of the starting compounds.

| BP. | 96° C./122 mbar |
|---|---|
| D.$_4^{20}$ | 0861 g/cm$^3$ |
| viscosity (20° C.) | 0.77 mPa.s. |

(C) Synthesis Cycle

The reactor contained the residue from the distillation, essentially 10 mols of 1-methoxy-propanol-2, largely reacted with sodium methylate. The molecular distillation head was replaced by a reflux condenser. 10 mols (902 g) of 1-methoxypropanol-2 were added so that the starting amount (20 mols) in step (A) was present. Boiling under reflux for 2 hours at 60° C./50 mbar resulted in a further 54 g of methanol being collected in the cooling trap. Then the product was reacted with methallyl chloride in analogy to (A) and worked up. 2382 g of distillate composed of 64% by weight 1-methoxy-2-methallyloxy-propane and 36% by weight 1-methoxypropanol-2 were obtained. 1414 g of pure product corresponding to a pure yield of 98% were isolated by continuing of the procedure in analogy to process sequence (B).

The synthesis-cycle according to (C) describes the reactor charge procedure for the repeated production of 1-methoxy-2-methallyloxy-propane.

EXAMPLE 2

Diethyleneglycol-monomethyl-monoallyl-ether (A) Synthesis 2020 g (16 mols) of diethyleneglycol-monomethyl-ether (MDG) and 449 g (8 mols of solid potassium hydroxide were introduced into the reaction vessel described in Example 1, but with a water-cooled reflux condenser (0.4 m$^2$ cooling area), N$_2$-blanket and 1-liter cooling trap (−80° C.) in advance of the vacuum production, and the pressure was reduced to 5 mbar. When heat was applied the reaction mixture began to boil at 44° C. and water split off, which under MDG-reflux was aspirated into the cooling trap (cooler escape temperature 17° C.) and was frozen there. After 200 minutes, a boiling temperature of 82° C. was reached and the potassium hydroxide had dissolved completely. After a further 180 minutes at 82° to 86° C. reactor temperature, the splitting off of water ceased. A total of 147 g of water was split off. Then, under normal pressure and thermostatic cooling at 50° C., 988 g (8 mols) of allyl bromide were metered into the reactor within 120 minutes. An exothermic reaction ensued, and the reactor temperature increased to 89° C., accompanied by potassium bromide precipitation. Stirring was continued for 60 minutes at 90° C. Then the reflux condenser was replaced by a distillation head for molecular distillation, and the product mixture consisting of 8 mols each of MDG and diethyleneqlycolmonomethyl-monoallylether was distilled off completely from the KBr-precipitate at 42° to 44° C./2 mbar. A total of 2202 g of distillate composed of 55% title compound and 45% MDG were obtained. 959 g of dry, pourable KBr were emptied out of the reactor.

(B) Isolation

The reactor described in part (A) of this example was charged with 2202 g of the final distillate from that procedure described in (A) and 449 g (8 mols) of solid potassium hydroxide. In analogy to (A), 109 g of water were split off within 280 minutes. After a further 2 hours it was found that in spite of incomplete reaction, no significant splitting off of water took place any longer. In total, only 126 g of water were obtained, that is, 88% of the amount of water to be expected. Thereupon, the reflux condenser was exchanged for a distillation head for molecular distillation, and 1020 g of diethyleneglycol-monomethyl-monoallyl ether were distilled off in pure form from the reaction mixture. This is 86% of the yield to be expected. The residual 14% were, for practical reasons, left in the reaction mixture for supporting the liquid consistency. They were recovered in the subsequent synthesis cycle.

| B.p. | 45° C. |
|---|---|
| D.$_4^{20}$ | 0.941 |
| Viscosity (20° C.) | 1.41 mPa.S. |

(C) Synthesis Cycle

The reactor contents after the final distillation of the process described in (B) above were, after exchange of the distillation head for the reflux condenser described in (A) above, augmented by addition of 8 mols (1010 g) of MDG to equal the quantity of starting material employed for the synthesis described in (A), and a residual 19 g of water were split off therefrom in 2 hours under reflux at 83° C. and 5 mbar. Then, the residue was reacted in the same way as in (A) with allyl bromide and worded up. 2400 g of distillate were obtained composed of 8% by weight total compound and 42% by weight MDG. 1157 g of pure title compound corresponding to a purity yield of 96% were isolated therefrom by continuing the process in the same way as in (B) above.

The synthesis cycle according to (C) describes the charging procedure for the repeated production of diethyleneglycol-monomethyl-monoallyl ether.

EXAMPLE 3

Triethyleneglycol-monomethyl-monoallyl ether (A) Synthesis

In analogy to Example (2A), 1970 g (12 mols) of triethyleneglycol-monomethyl ether (MTG) and 240 g (6 mols) of solid sodium hydroxide were converted into the alcoholate at 2 mbar by heating at 110° C. and splitting of water. The splitting off of water began at 40° C. and ceased after the discharge of 110 g of water after 6 hours. Then 460 g (6 mols) of allyl chloride were metered in at 70° C. controlled temperature within 50 minutes, whereby the reactor temperature increased to 90° C. and sodium chloride precipitated out. Molecular distillation at 90° to 93° C./2 mbar yielded 2191 g of an equimolar mixture consisting of 44% methyltriglycol and 56% triethyleneglycol-monomethylmonoallyl ether. The distillation residue consisted of 362 g of dry, pourable NaCl.

(B) Isolation

In analogy to Example (2B), 91 g of water were split off from 2191 g of final distillate from reaction sequence (A) above and 240 g (6 mols) of solid NaOH, that is, 84% of the amount of water to be expected, within 330 minutes. Then, 942 g of pure triethyleneglycol-monomethyl-monoallyl ether were distilled off from the reaction mixture (B.p. 84° C./1 mbar), that is, 77% of the yield to be expected. The remaining 23% of the yield were left in the reaction mixture to maintain a liquid consistency. They were recovered in the subsequent synthesis cycle.

| B.p. | 84° C./1 mbar |
|---|---|
| $D_4^{20}$ | 0.975 |
| Viscosity (20° C.) | 2.69 mPa.s. |

(C) Synthesis Cycle

The reactor contents were, in the same way as in Example (2C), after addition of a further 6 mols (985 g) of MTG, freed from residual water (20 g) at 110° C./2 mbar in 160 minutes whereby the alcoholate production was concluded, reacted in the same way as in (A) above with 460 g (6 mols) of allyl chloride and worked up. 2478 g of distillate were obtained composed of 61% by weight title compound and 39% by weight MTG. 1146 g of pure title compound corresponding to a pure yield of about 94%, were isolated therefrom by continuing the process in the same way as in part (B) above.

The synthesis cycle according to (C) describes the charging procedure for the repeated production of triethyleneglycolmonomethyl-monoallyl ether.

EXAMPLE 4

Triethyleneglycol-monomethyl-monomethallyl ether (A) Synthesis

The suction side of a Roots pump (suction performance 30 m³/h) was connected to the apparatus described in Example (2A) at the reflux condenser, and the pressure side of the pump was connected via a cooling water-driven vapor condenser (0.4 m² exchange surface) with a pre-vacuum pump adjusted to 35 mbar.

The apparatus was charged with 1970 g (12 mols) of triethyleneglycol-monomethyl ether (MTG) and 480 g (6 mols) of 50% by weight aqueous sodium hydroxide. Within about 260 minutes, 320 g of water were withdrawn with the beginning of boiling at 38° C. and slowly increasing temperature to 82° C. Within a further 100 minutes with further temperature increase to 110° C., a further 22 g of water were withdrawn; and finally within a further 40 minutes, a further 10 g of water were withdrawn while maintaining 110° C. The total splitting off of water amounted to 352 g. In the same way as in Example (2A), the reactor contents were then reacted at 80° C. controlled temperature within 80 minutes with 543 g (6 mols) of methallyl chloride. Molecular distillation at 90°-92° C./2 mbar yielded 2283 g of an equimolar mixture of 57% triethyleneglycol-monomethylmonomethallyl ether, 43% of MTG and 365 g NaCl.

(B) Isolation

In the same way as in Example (2B), although with the vacuum arrangement described in (A) above, 93 g of water were split off from the distillate obtained in (A) and 240 g 6 mols) of solid NaOH within 20 minutes, that is, 86% of the amount of water to be expected. Then, 969 g of pure triethyleneglycol-monomethylmonomethallyl ether (B.p. 89° C./1 mbar) were distilled out of the reaction mixture, that is, 74% of the theoretical yield. The remaining 26% of the yield to be expected were left in the reaction mixture to maintain a liquid consistency. They were recovered in the subsequent synthesis cycle.

| B.p. | 89° C./1 mbar |
|---|---|
| $D_4^{20}$ | 0.965 g/cm³ |
| Viscosity (20° C.) | 2.94 mPa.s. |

(C) Synthesis Cycle

The reactor contents from the isolation process in (B) above were freed from residual water in 17 minutes in the same way as in (A) after addition of further 6 mols (985 g) of MTG, and reacted again with 543 g (6 mols) of methallyl chloride and worked up. 2162 g of an equimolar mixture composed of 59% by weight title compound and 41% by weight methyltriglycol were obtained as distillate. 1230 g of pure title compound, corresponding to a pure yield of 94%, were isolated therefrom by continuing the process in the same way as in (B) above.

Cycle (C) can be repeated as in the foregoing Examples.

EXAMPLE 5

Triethyleneglycol-monobutyl-monoallyl-ether (A) Synthesis

In the same way as in Example (2A), 2063 g (10 mols) of triethyleneglycol-monobutyl ether (BTG) were converted into the alcoholate within 5 hours at 2 mbar and 115° C. with release of 93 g of water, and the alcoholate was reacted with 383 g (5 mols) of allyl chloride as in Example (3A). Distillation yielded 2243 g of a mixture of 55% title compound and 45% BTG, as well as 300 g of NaCl.

(B) Isolation

In the same way as in Example (2B), 70 g of water (78% of the amount to be expected with complete reaction) were split off from the distillate obtained in (A) and 200 g of NaOH within 220 minutes. Then, 841 g of pure triethyleneglycol-monobutyl-monoallyl-ether were distilled out of the reaction mixture, that is, about 68% of the total yield. The remaining yield was isolated in synthesis cycle (C).

| B.p. | 92° C./1 mbar |
|---|---|
| $D_4^{20}$ | 0.941 |
| Viscosity (20° C.) | 3.56 mPa.s |

(C) Synthesis Cycle

The reactor contents from (B) were, in the same way as in Example (2C), freed from residual water (20 g) after addition of a further 5 mols (1032 g) BTG at 115° C./2 mbar in 150 minutes, reacted again with 5 mols (383 g) of allyl chloride analogous to (A) and worked up. About 2640 g of distillate were obtained (mixture of 61% by weight title compound and 39% by weight TBG). 1114 g of triethyleneglycol-monobutyl-monoallyl-ether corresponding to a pure yield of 90% were isolated therefrom by continuing the process as described in (B) above.

Cycle (C) was repeated.

EXAMPLE 6

Tetraethyleneglycol-monomethyl-monoallyl-ether (A) Synthesis

In the same way as in Example (2A), 2083 g (10 mols) of tetraethyleneglycol-monomethyl-ether (MTeG) and 200 g (5 mols) of NaOH were converted into the alcoholate within about 6 hours at 2 mbar and 118° C. with release of 92 g of water and the alcoholate was reacted with 383 g (5 mols) of allyl chloride. Distillation yielded 2266 g of a mixture of 45% MTG and 55% tetraethyleneglycol-monomethyl-monoallyl-ether, in addition to 300 g of NaCl.

(B) Isolation

In the same way as in Example (2B), 75 g of water (about 83% of the amount to be expected with complete reaction) were split off from the distillate obtained in (A) above and 300 g of NaOH within 240 minutes. Then 868 g of pure tetraethyleneglycol-monomethyl-monoallyl-ether were distilled out of the reaction mixture. This is 70% of the total yield to be expected. The residual 30% was recovered in the subsequent synthesis cycle.

| B.p. | 98° C./1 mbar |
| $D_4^{20}$ | 1/003 g/cm$^3$ |
| Viscosity (20° C.) | 4.49 mPa.s. |

(C) Synthesis Cycle

The reactor contents from (B) above were freed from residual water (17 g) in the same way as in Example (2C), after addition of a further 5 mols (1042 g) of methyltetraglycol, at 118° C./1 mbar in 140 minutes, and reacted again with 5 mols (383 g) of allyl chloride. 2635 g of distillate were obtained (mixture of 61% by weight title compound and 39% by weight MTeG). 1127 g of pure product, corresponding to a pure yield of 92%, were isolated therefrom by continuing the process in the same way as described in (B) above.

Cycle (C) was repeated.

EXAMPLE 7

Tetraethyleneglycol-monoethyl-monoallyl-ether (A) Synthesis

In the same way as in Example (6A), 1780 g (8 mols) of tetraethyleneglycol-monomethyl-ether (ETeG) and 160 g (4 mols) of solid NaOH were converted into the alcoholate at 1 mbar and 114° C. with release of 73 g of water, and the alcoholate was reacted with 306 g 4 mols) of allyl chloride in the same way as in Example (6A). Distillation yielded 1924 g of a mixture of 46% ETeG and 54% tetraethyleneglycol-monoethyl-monoallyl-ether, in addition to 240 g NaCl.

(B) Isolation 59 g of water (81% of the total amount) were obtained with 160 g (4 mols) NaOH and the foregoing distillate. Then 735 g of pure tetraethyleneglycol-monoethylmonoallyl-ether were distilled out of the reaction mixture. This is 70% of the total yield to be expected. The remaining yield was recovered in the subsequent synthesis cycle.

| B.p. | 106° C./0.5 mbar |
| $D_4^{20}$ | 0.971 |
| Viscosity (20° C.) | 4.41 mPa.s. |

(C) Synthesis Cycle

Again, in the same way as in Example (6C), the remaining water (about 15 g) was removed after addition of 4 mols (890 g) of ETeG, and the residue was reacted with 4 mols (306 g) of allyl chloride. Working up yielded 2224 g of distillate which contained 61% by weight title compound in addition to ethyltriglycol. 964 g of tetraethyleneglycol-monoethyl-monoallyl-ether, which corresponds to a total yield of 92%, were isolated therefrom by continuing the process in the same way as in (B) above.

The synthesis cycle according to (C) was repeated.

EXAMPLE 8

Pentaethyleneglycol-monomethyl-monoallylether (A) Synthesis

In the same way as in Example (6A), 1514 g (6 mols) of pentaethyleneglycol-monomethyl-ether (MPG) and 120 g (3 mols) of solid sodium hydroxide were converted into the alcoholate at 1 mbar and 120° C. with release of 56 g of water, and the alcoholate was reacted with 230 g (3 mols) of allyl chloride. Distillation yielded 1620 g of a mixture consisting of 54% pentaethyleneglycol-monomethyl-monoallyl-ether in addition to methylpentaglycol, and 180 g NaCl.

(B) Isolation 43 g of water (80% of the total amount) were split off from the aforementioned distillate and 120 g (3 mols) of NaOH. Then, 571 g of pure pentaethyleneglycol-monoethyl-monoallyl-ether were distilled out of the reaction mixture. This is 65% of the total yield. The remaining amount was recovered in the subsequent synthesis cycle.

| B.p. | 114° C./0.6 mbar |
| $D_4^{20}$ | 1.020 |
| Viscosity (20° C.) | 6.35 mPa.s |

(C) Synthesis Cycle

Again, in the same way as in Example (6C), the residual water (about 12 g) was split off after addition of 3 mols (757 g) MPG to the reactor contents, and the residue was reacted with 3 mols (230 g) of allyl chloride. Working up yielded 1919 g of distillate containing 61% by weight of title compound in addition to methylpentaglycol. In the same way as in (B) above, 797 g of pentaethyleneglycol-monoethyl-monoallyl-ether were isolated therefrom by continuing the process as in (B) above, which corresponds to a total yield of 91%.

Cycle (C) was repeated.

EXAMPLE 9

Tetraethyleneglycol-monobutyl-monoallyl-ether

In the same way as in Example 6, tetraethyleneglycol-monobutyl-monoallyl-ether was produced from butyltetraglycol, sodium hydroxide and allyl chloride with a 94% yield.

| B.P. | 122° C./1 mbar |
|---|---|
| $D_4^{20}$ | 0.966 |
| Viscosity (20° C.) | 5.48 mPa.s. |

EXAMPLE 10

Triethyleneglycol-monomethyl-monovinyl-ether

In the same way as in Example 1, the title compound was produced in a 1-liter apparatus from 2 molar starting mixture of methyltriglycol, with precipitation of NaBr.

| B.p. | 76° C./1 mbar |
|---|---|
| $D_4^{20}$ | 1.047 |
| Viscosity (20° C.) | 6.85 mPa.s. |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an asymmetric terminally monounsaturated glycol ether of the formula $$R_1-(O-R_3)_n-OR_2 \tag{I}$$

wherein
$R_1$ is straight or branched alkyl of 1 to 4 carbon atoms,
$R_2$ is terminally unsaturated alkenyl of 2 to 6 carbon atoms, optionally methyl- or ethyl-substituted,
$R_3$ is identical or different alkylene groups of 2 to 4 carbon atoms, optionally methyl- or ethyl-substituted, and
n is an integer from 1 to 6, inclusive, by converting a monoalkyl ether of the formula $$R_1-(O-R_3)_n-OH \tag{II}$$

wherein $R_1$, $R_3$ and n have the meanings previously defined, into an alcoholate with the aid of an alkali metal or alkaline earth metal or an alcoholate, oxide, hydride or hydroxide thereof, and subsequently reacting the alcoholate with a terminally unsaturated alkenyl halide of the formula $$X-R_2 \tag{III}$$

wherein
X is chlorine, bromine or iodine, and
$R_2$ has the meanings previously defined, which comprises
(a) reacting two equivalents of (II) with one equivalent of the alcoholate-forming metal component under exclusion of oxygen until its complete conversion into the alcoholate and distilling off the respective labile group,
(b) completely reacting the (II)-alcoholate with one equivalent of (III),
(c) separating the mixture of substances (I) and (II) formed thereby from the precipitated metal halide by filtration or distillation,
(d) reacting the distillate or filtrate with a second equivalent of the alcoholate-former under the conditions of (a),
(e) distilling off the major amount of (I) in the reaction mixture, and
(f) adding another equivalent of (II) to the alcoholate-containing reaction mixture remaining behind after the recovery of (I), allowing the reaction according to (a) to go to completion, and repeating the process steps (a) to (e).

2. The method of claim 1, wherein the process temperature is limited at all times to a maximum of 130° C.

3. The method of claim 1, wherein the process temperature is limited to 110° C.

4. The method of claim 1, wherein the process step (a) is performed at the boiling point.

* * * * *

UNITED STATES PATENT AND TRADEMARK OFFICE
CERTIFICATE OF CORRECTION

PATENT NO. : 4,987,268
DATED : January 22, 1991
INVENTOR(S) : Hartwig Rauleder et al It is certified that error appears in the above-identified patent and that said Letters Patent is hereby corrected as shown below:

Column 5, line 14, "220 g of 1methanol" should read
--220 g of methanol--.

Column 6, line 15, "diethyleneqlycolmonomethyl"

should read --diethyleneglycolmonomethyl--.

Column 6, line 56, "8%" should read --58%--.

Signed and Sealed this

Twentieth Day of October, 1992

Attest:

DOUGLAS B. COMER

Attesting Officer  Acting Commissioner of Patents and Trademarks